United States Patent [19]

Hasegawa et al.

[11] Patent Number: 4,807,606

[45] Date of Patent: Feb. 28, 1989

[54] THERAPEUTIC APPLIANCE FOR IMPROVING FUNCTIONS OF HAND FINGERS

[75] Inventors: Tsuneo Hasegawa; Mitsuma Matsumura; Atsuki Hashimoto; Toshio Mikiya, all of Tokyo, Japan

[73] Assignee: Nitto Kohki Co., Ltd., Tokyo, Japan

[21] Appl. No.: 86,819

[22] Filed: Aug. 19, 1987

[30] Foreign Application Priority Data

Sep. 22, 1986 [JP] Japan ................................ 61-145333

[51] Int. Cl.[4] ............................ A61F 5/10; A61H 9/00

[52] U.S. Cl. ................................ 128/77; 178/DIG. 20

[58] Field of Search ..................... 128/77, 26, DIG. 20

[56] References Cited

U.S. PATENT DOCUMENTS

| | | | |
|---|---|---|---|
| 2,880,721 | 4/1959 | Corcoran | 128/26 |
| 3,457,912 | 7/1969 | Clark et al. | 128/26 |
| 3,581,740 | 6/1971 | Sherbourne | 128/77 |
| 3,937,215 | 2/1976 | Barthlome | 128/26 |
| 4,173,218 | 11/1979 | Cronin | 128/77 |
| 4,274,399 | 6/1981 | Mammert | 128/26 |
| 4,522,197 | 6/1985 | Hasegawa | 128/26 |
| 4,596,240 | 6/1986 | Takahashi et al. | 128/26 |
| 4,619,250 | 10/1986 | Hasegawa | 128/26 |
| 4,671,258 | 6/1987 | Barthlome | 128/26 |
| 4,706,658 | 11/1987 | Cronin | 128/77 |

FOREIGN PATENT DOCUMENTS

| | | | |
|---|---|---|---|
| 735700 | 6/1966 | Canada | 128/DIG. 20 |
| 2126110 | 3/1984 | United Kingdom | 128/26 |
| 2147812 | 5/1985 | United Kingdom | 128/26 |

*Primary Examiner*—Edgar S. Burr
*Assistant Examiner*—Tonya Lamb
*Attorney, Agent, or Firm*—Staas & Halsey

[57] ABSTRACT

A hand therapeutic appliance, including: a splint cloth with a portion for accommodating a palm with the fingers spread apart, and a portion for covering the underside surface of the carpal joint and forearm; retainers for releasably holding the five spread apart fingers; retainers for releasably securing the wrist and/or forearm to the forearm splint portion; a plurality of first generally delta-shaped pockets positioned between adjacent fingers; a pair of second pockets extending from the finger tips toward the forearm along substantially the full length of the splint cloth, the second pockets span the space between the thumb and the forefinger and the space between the ring finger and the middle finger, respectively; a pair of third generally delta-shaped pockets, one of the third pockets extending between the pair of second pockets from the finger tips toward the wrist to span the forefinger and the middle finger, and the other of the third pockets extending from the finger tips toward the wrist to span the ring finger and the little finger; a plurality of inflatable bladders, each accommodated within a first, second or third pocket; tubes for inflating and deflating the bladders; and darts provided at the pair of second pockets at locations corresponding generally to the wrist to facilitate bending of the second pockets back toward the palm side when the bladders within the pockets are inflated.

4 Claims, 7 Drawing Sheets

THERAPEUTIC APPLIANCE FOR IMPROVING FUNCTIONS OF HAND FINGERS

BACKGROUND OF THE INVENTION

This invention relates to a therapeutic appliance for aiding in recovering the functions of carpal joints, hands and fingers incapacitated due to diseases or impediments in the central nervous system, such as cerebrovascular troubles, cerebral injury, cerebral palsy and spinal damage, as well as impediments in the peripheral nervous system, joints, muscles, and tendons.

In the event that the forearms, carpal joints, hands and fingers are functionally disordered due to the foregoing diseases and impediments, it is required to conduct exercise for recovering mobility concurrently with medical treatment. However, it has been heretofore recognized very difficult to recover the functions of incapacitated carpal joints, hands and fingers. No satisfactory therapeutic appliance for recovering the functions has yet been developed for all research in the modern rehabilitative medicine. For example, many conventional therapeutic appliances utilizing air pressure or spring actions to aid in restoring the extensibility of carpal joints, hands and fingers inflicted with bending contracture or dysfunction in extending motion have produced no satisfactory results in that they involve complicated motions and impose excessive burdens on patients.

In this regard the present inventors have proposed a therapeutic appliance for improving functions of hand fingers as disclosed in U.S. Pat. No. 4,619,250. The appliance of said patent application comprises a palm splint cloth shaped so as to accommodate a hand with its fingers spread apart. Finger retainer members are disposed on the front surface of the splint cloth for holding the fingers individually in their spread apart positions. A plurality of first bladders is disposed on the front surface of said palm splint cloth and positioned between adjacent fingers, except between the thumb and forefinger, for spreading the fingers apart from each other. A plurality of second bladders is disposed on the opposite surface of said palm splint cloth for extending the fingers, hand and carpal joint. Fluid (air) supply and discharge tubes are connected to the first and second bladders for supplying and discharging fluid to and from the bladders. Compressed air is supplied to the bladders through the tubes and discharged from the bladders through the tubes. This operation may be repeated to impart extending and opening motions to the functionally incapacitated carpal joint, hand and fingers intermittently and rythmically to thereby remedy the bending contracture and dysfunction in extending motion as well as to create a motive for triggering self-motivating capacity. This appliance has provided drastically excellent effects in improving functions of hands and fingers by using a flat palm-shaped splint cloth, rather than the conventional glove-type splint, and finger retainers for holding the fingers individually to make it easy for a patient to wear the appliance on his or her bent and contractured fingers and by disposing bladders between adjacent fingers to effectively spread the fingers apart in addition to extending the fingers, in contrast to the prior art glove-type appliance. The therapeutic appliance disclosed in the aforesaid patent application has thus gained favorable reception in the medical field.

However, the present inventors are still not totally satisfied with this appliance in that it does not provide sufficient bending of the patient's carpal joint towards the back of the hand.

SUMMARY OF THE INVENTION p Accordingly, a primary object of this invention is to provide a novel therapeutic appliance for improving the functions of incapacitated hands and fingers which is equipped with means for bending the carpal joint towards the back of the hand to thereby induce voluntary motions more effectively.

Briefly, the present invention consists of a therapeutic appliance for improving the functions of a person's carpal joints, hands and fingers including:

a splint cloth made of flexible material including a palm splint portion so shaped as to accommodate a palm with its fingers spread apart, and a forearm splint portion extending from the palm splint portion so as to cover the underside surface of the carpal joint and forearm;

finger retainer means disposed on the hand back side surface of said palm splint portion for releasably holding the five fingers individually in their spread apart positions;

wrist and/or forearm retainer means on said forearm splint portion for releasably securing the wrist and/or forearm to the forearm splint portion;

a plurality of first generally delta-shaped pockets made of substantially non-extensible material disposed on the hand back side surface of said palm splint portion so as to be positioned between adjacent fingers;

a pair of second pockets made of substantially nonextensible material disposed on the palm side surface of said splint cloth and extending in generally parallel relation to each other from the finger tips toward the forearm along substantially the full length of the splint cloth, said second pockets positioned so as to span the space between the thumb and the forefinger and the space between the forefinger and the middle finger, respectively;

a pair of third generally delta-shaped pockets made of substantially non-extensible material disposed on the palm side surface of said palm splint portion, one of said third pockets extending between said pair of second pockets from the finger tips toward the wrist so as to span the forefinger and the middle finger, and the other of said third pockets extending from the finger tips toward the wrist so as to span the ring finger and the little finger;

a plurality of inflatable bladders, one accommodated within each of said first, second and third pockets; and fluid supply and discharge tubes connected to said bladders for supplying and discharging fluid at a predetermined pressure to and from said bladders. Said pair of second pockets is provided with darts or gussets at locations corresponding generally to the wrist so as to facilitate bending of said second pockets back toward the palm side when the bladders within said pockets are inflated with fluid.

In one embodiment of the invention a wrist pillow may be detachably secured to the hand back side surface of the forearm splint portion at a location corresponding to the wrist to hold the wrist and forearm fixed in place to the appliance.

In another embodiment of this invention, a palm pad may be detachably secured to the hand back side surface of said palm splint portion so as to fit the hollow of the palm to aid in transmitting the action of the pockets when expanded to the palm.

BRIEF DESCRIPTION OF THE DRAWINGS

Specific embodiments of the invention will now be described by way of example and not by way of limitation with reference to the accompanying drawings, in which.

DESCRIPTION OF THE EMBODIMENT

Figure 1:
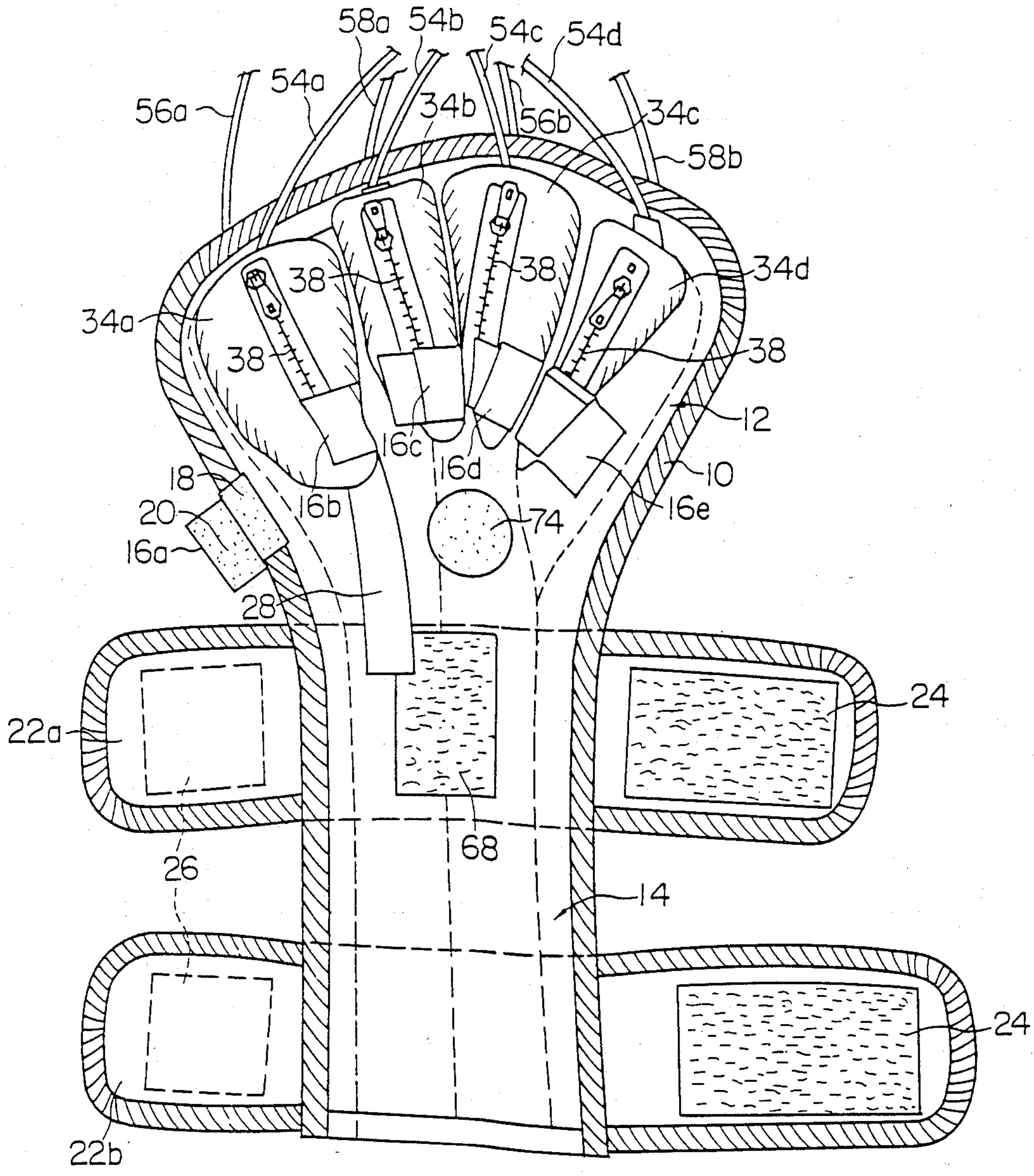
FIG. 1 is a rear view of the therapeutic appliance according to one embodiment of this invention as viewed from the hand back side.

FIG. 1 is a rear view of the therapeutic appliance for the right hand according to one embodiment of the present invention. The therapeutic appliance includes a base cloth or splint cloth 10 having air bladders disposed on both the palm and back sides thereof. The splint cloth 10 is composed of two portions, a palm splint portion 12 so shaped as to accommodate the entire palm of a standard size hand of a healthy person with its five fingers spread apart and a forearm splint portion 14. The splint cloth 10 may be made of pliable and agreeable-to-the touch, flexible material such as woven fabric, knit fabric, unwoven fabric, air-permeable synthetic resin sheets or the like.

The palm splint portion 12 is provided on its palm side surface with "VELCRO" or hook and loop fastener type finger retainer means 16*a*, 16*b*, 16*c*, 16*d* and 16*e* for releasably holding the five fingers individually to the palm splint portion in their spread apart position. As shown in FIG. 1, each of the finger retainer means 16*a*–16*e* comprises a pair of strips, one having a looping element 18 of a VELCRO fastener on its free end and the other having a mating hooking element 20 of the VELCRO fastener on its free end to tie the strips up into a loop.

The forearm splint portion 14 is provided with wrist retainer means 22*a* and arm retainer means 22*b* for holding the wrist and forearm respectively to the forearm splint portion 14. Each of the retainer means 22*a* and 22*b* includes a pair of opposed straps, one having a looping element 24 of a Velcro fastener on its free end and the other having a mating hooking element 26 of the VELCRO fastener on its free end to tie the straps together in a loop.

Figure 9:
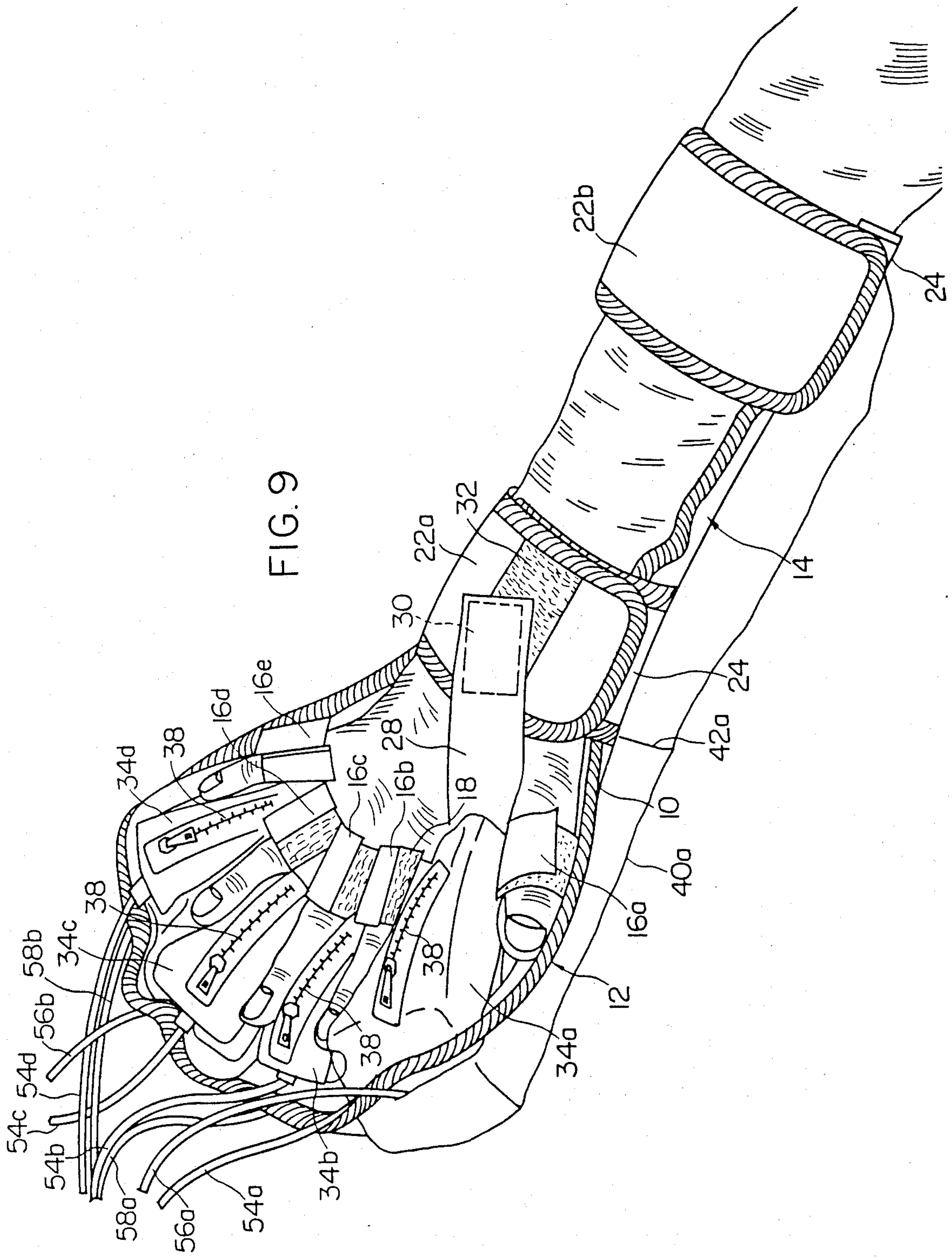
FIG. 9 is a perspective view of the therapeutic appliance applied to the patient's hand with all of the pockets partially inflated with air.

As shown in FIGS. 1 and 9, a bracer band 28 is affixed at its one end to the back side of the palm splint portion 12 at the root between the thumb and the forefinger and extends obliquely and rearwardly such that a hooking element 30 attached to the other free end is engageable with a mating loping element 32 secured to the outer surface of the strap of the wrist retainer means 22*a* to hold the palm of a patient hand closely against the splint cloth 10.

Figure 3B:
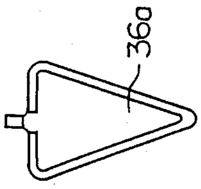
FIG. 3B is a plan view of the second bladder disposed between the third and fourth fingers.
Figure 3A:
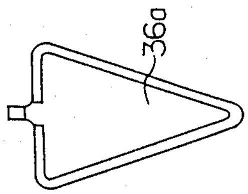
FIG. 3A is a plan view of the first bladder disposed between the second and third fingers.

Three-dimensional delta-shaped pockets 34*a*, 34*b*, 34*c* and 34*d* are disposed on the hand back side of the palm splint portion 12 between each of the adjacent finger retainers 16*a*, 16*b*, 16*c*, 16*d*, 16*e* to maintain the five fingers in their spread apart position as shown in FIG. 9. The delta-shaped pockets 34*a*–34*d* are sized to fit the spaces between the fingers and expanded in a delta shape toward the finger tips while the rear ends of the pockets extend between the finger retainer means 16*a*–16*e*. Accommodated within each of the pockets 34*a*–34*d* is an inflatable air bladder 36*a* adapted to be inflated with compressed air as shown in FIGS. 3A and 3B. The bladders 36*a* are formed of an appropriate air-impermeable sheet such as plastic sheet material. The bladders assume a triangular shape in their flat contracted state as shown in FIGS. 3A and 3B. The bladder shown in FIG. 3A is for use between the thumb and forefinger and is bigger in size than the bladder shown in FIG. 3B which is for use in the spaces between the forefinger and middle finger, between the middle finger and ring finger, and between the ring finger and little finger, which spaces are smaller than the space between the thumb and forefinger. As the bladders 36*a* are inflated with compressed air, the bladders are restrained from being expanded to an excessive extent by the inner wall surfaces of the respective pockets 34*a*–34*d* and thereby maintained in their defined shape conforming with the shape of the interiors of the corresponding pockets 34*a*–34*d*.

Each of the pockets 34*a*–34*d* is closed by zippers 38 so as to provide accessibility to the interior of the pocket when there is a need to replace the bladder 36*a* with a new one, for example.

Figure 2:
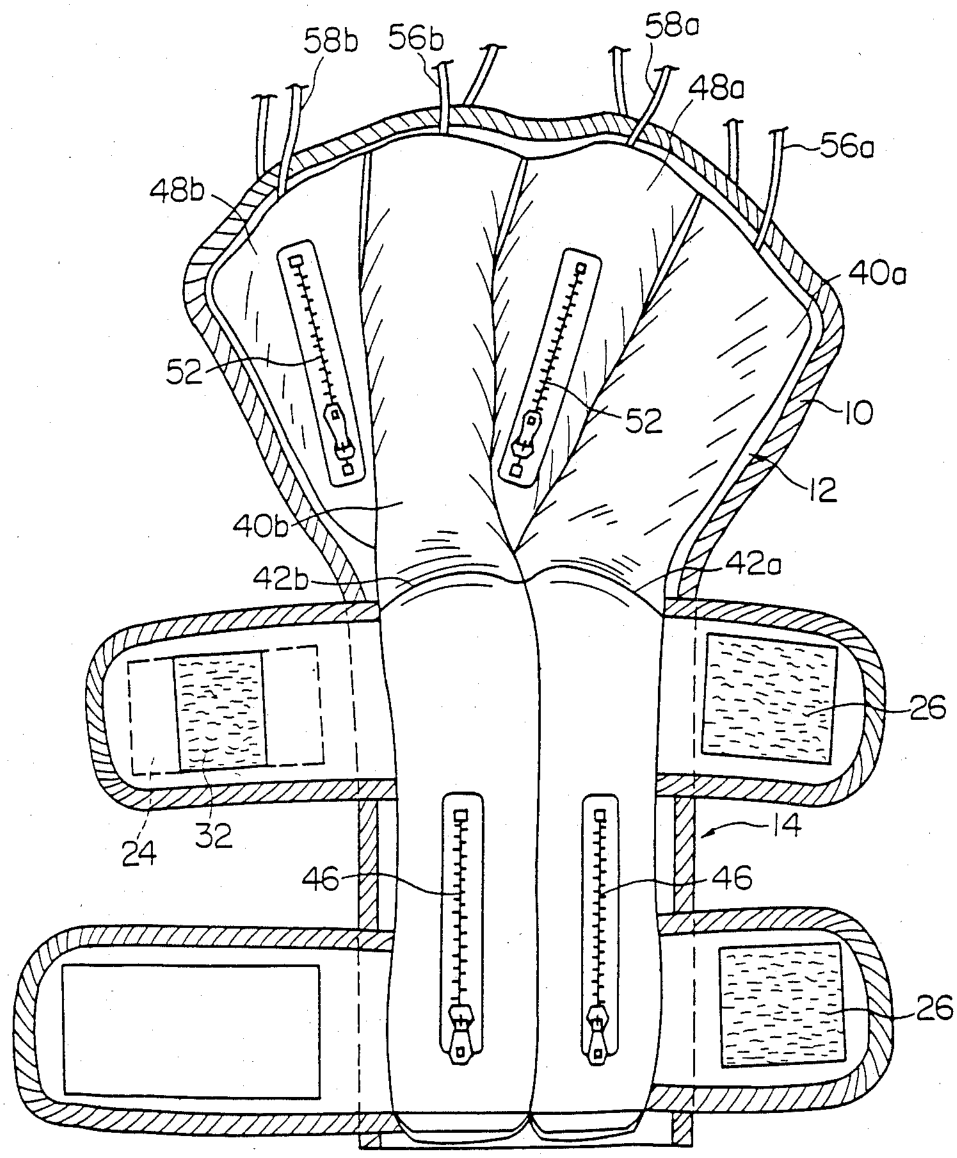
FIG. 2 is a front view of the appliance shown in FIG. 1 as viewed from the hand palm side.

As shown in FIG. 2, the splint cloth 10 further includes a pair of pockets 40*a*, 40*b* made of substantially non-extensible, pliable material extending longitudinally along substantially the full length of the splint cloth 10 including the palm splint portion 12 and forearm splint portion 14. One of the pockets 40*a* spans the thumb and the forefinger and extends from the finger tip towards the forearm. The other pocket 40*b* spans the middle finger and the ring finger and extends from the finger tip towards the forearm. The pockets 40*a* and 40*b* extend in back-to-back relation with the pockets 34*a* and 34*c*, respectively. The pockets 40*a*, 40*b* are each a three-dimensionally sewn bag provided with transverse darts 42*a*, 42*b*, respectively, at the location corresponding to the carpal joint or wrist intermediate the opposite ends of the pockets so that the pockets may be bent angularly backward (into the shape of a V). Thus, the pockets 40*a*, 40*b* are positively bent towards the back of the hand in a shallow V-shape when expanded by air bladders 44*a* (which will be described later), whereby the splint cloth 10 is forcedly bent backwardly in a shallow V-shape. The darts 42*a*, 42*b* may be replaced by gussets (not shown), although gussets are not recommended because of the cost.

Figure 4:
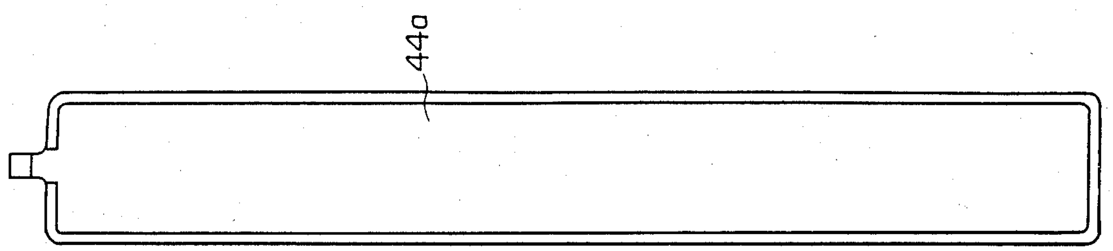
FIG. 4 is a plan view of the bladder for accommodating the first and second pockets.

Housed within each of the pockets 40*a*, 40*b* is an inflatable air bladder 44*a* as shown in FIG. 4 which is similar to the bladder 36*a*. The bladders 44*a* assume a rectangular shape in their flat contracted state as shown in FIG. 4 and are accommodated in the flat state in the respective pockets 40*a*, 40*b*. As the bladders 44*a* are inflated with compressed air, they are restrained from being expanded to an excessive or unnecessarily great extent by the inner wall surfaces of the pockets 40*a*, 40*b* and thereby maintained in their defined shape conforming with the shape of the corresponding pockets 40*a*, 40*d*.

Each of the pockets 40*a*, 40*b* can be opened by zippers 46 so as to provide accessibility to the interior of the pockets to insert and remove the bladders 44*a* into and from the pockets.

Figure 5:
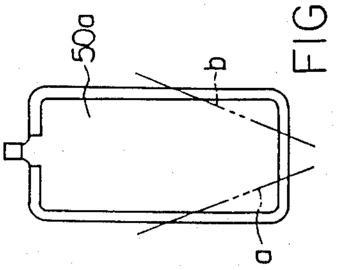
FIG. 5 is a plan view of the bladder for accommodating the third and fourth pockets.

The splint cloth 10 includes another pair of delta-shaped pockets 48*a* and 48*b* on the palm side of the palm splint portion 14. The pockets 48*a*, 48*b* are three-dimensional bags formed of the same material as the pockets 40*a*, 40*b*. One of the delta-shaped pockets 48*a* spans the forefinger and middle finger between the other pair of pockets 40*a* and 40*b* in back-to-back relation with the delta-shaped pocket 34*b*, and extends from the finger crotch to the finger tip. The other pocket 48*b* spans the ring finger and little finger in back-to-back relation with the delta-shaped pocket 34*d*, and diverges as it extends from the finger crotch to the finger tip. The boundary line between the pockets 40*a* and 48*a* lies generally on the central longitudinal line of the forefinger when the fingers are in their spread apart position. The boundary line between the pockets 48*a* and 40*b* lies generally on the central longitudinal line of the middle finger. The boundary line between the pockets 40*b* and 48*b* lies generally on the central longitudinal line of the forefinger. Housed within each of the pockets 48*a*, 48*b* is an inflatable air bladder 50*a* as shown in FIG. 5 which is similar to the bladder 36*a*. The bladders 50*a* are formed of a plastic sheet material as the bladders 44*a* are. The bladders 50*a* assume a rectangular shape in their flat contracted or deflated condition and are accommodated in the respective pockets 48*a*, 48*b* with their lower opposed corners folded in as shown in dotted lines a and b in FIG. 5. As the bladders 48*a*, 48*b* are inflated with compressed air, they are retained from being expanded to an excessive or unnecessarily great extent by the inner walls of the pockets 48*a*, 48*b* and maintained in their defined shape generally conforming with the shape of the pockets 48*a*, 48*b*. It is to be noted that the bladders 50*a* exert greater pneumatic actions in lateral or transverse directions on the pockets than in other directions since the bladders 50*a* are of rectangular shape whereas the pockets are triangular in shape.

The pockets 48*a*, 48*b* can also be opened by zippers 52.

Connected to the bladders 36*a* in delta-shaped pockets 34*a*–34*d* are air tubes 54*a*, 54*b*, 54*c* and 54*d* as shown in FIG. 1. Air tubes 56*a* and 56*b* are connected to the bladders 44*a* in the pockets 40*a* and 40*b*, respectively. Connected to the bladders 50*a* in the pockets 48*a* and 48*b* are air tubes 58*a* and 58*b*.

All of these air tubes 54*a*–54*d*, 56*a*, 56*b*, and 58*a*, 58*b* are connected to a compressed air source 64 by means of a pair of air supply and discharge headers 60 and a pair of air hoses 62. Compressed air at a predetermined pressure from the source 64 is thus supplied simultaneously into all of the bladders. And the compressed air is forcedly discharged simultaneously from the bladders back into the source 64 via the air tubes. When it is desired to supply compressed air selectively into the bladders 36*a*, 44*a* and 50*a*, one or more of the air tubes 54*a*–54*d*, 56*a*, 56*b*, 58*a* and 58*b* leading to the bladder or bladders which need not be supplied with compressed air may be closed to interrupt the supply of air by, e.g., pinching the tube or tubes by a clip (not shown).

Figure 6:
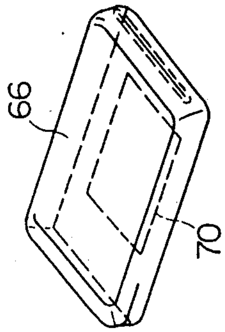
FIG. 6 is a perspective view of the wrist pillow.

As shown in FIG. 6, a relatively firm flat wrist pillow 66 may be provided which is adapted to be interposed between the forearm splint portion 14 and the underside of the patient's wrist to ensure closer contact of the forearm splint portion 14 of the splint cloth 10 against the underside of the wrist to thereby more positively transmit the action of the expanded pockets 40*a*, 40*b* to the carpal joint. The pillow 66 may be adjusted in position and fastened to the forearm splint portion 14 at the location corresponding to the wrist retainer means 22*a* by means of a looping element 68 of a VELCRO fastener on the splint portion 14 and a mating hooking element 70 on the underside of the pillow 66.

Figure 7A:
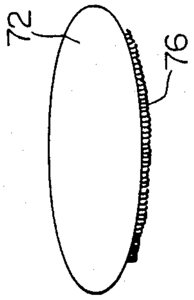
FIGS. 7A and 7B are side and plan views, respectively, of the mat for the hollow of the palm.
Figure 7B:
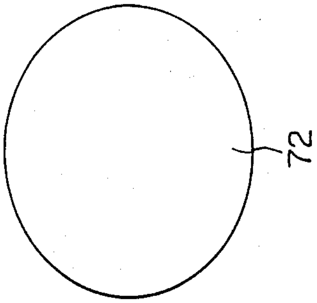
Figure 8:
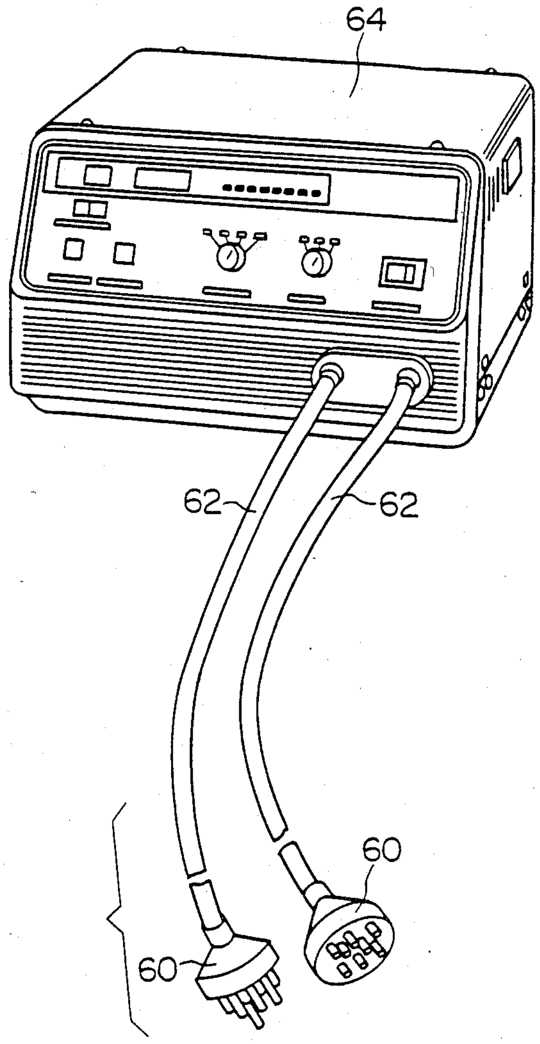
FIG. 8 is a perspective view of the source of compressed air.

Referring to FIGS. 7A and 7B, a flat palm pad or mat 72 which is as firm as or slightly firmer than the wrist pillow 66 may be inserted between the hand back side of the palm splint portion 12 and the palm of a patient so as to be applied to the hollow of the palm whereby closer contact of the palm splint portion 12 against the hollow of the palm may be ensured to more positively transmit the action of the expanded pockets 40*a*, 40*b* to the carpal joint. The palm pad 72 may be adjusted in position and fastened to the hand back side of the palm splint portion 12 at the location corresponding to the hollow of the palm by means of a looping element 74 of a VELCRO fastener on the palm splint portion 12 and a mating hooking element 76 on the pad 72.

Alternatively, the pad 72 may be substituted for by one or more inflatable air bladders which are adapted to be inflated and deflated in synchronization with inflation and deflation of the bladders 44*a* in the pockets 40*a*, 40*b*. The term "mat" or "pad" herein used is thus intended to include inflatable air bladders as well.

The operation of the therapeutic appliance according to this invention will be described below.

Prior to applying the therapeutic appliance to the functionally incapacitated hand, fingers and forearm, the finger retainer means 16*a*–16*e* disposed on the hand back side of the palm splint portion 12 and the wrist and forearm retainer means 22*a*, 22*b* are opened, and the wrist pillow 66 is secured to the forearm splint portion 14 at a location, corresponding to the wrist by means of the VELCRO fastener 68, 70.

The hand back side of the palm splint portion 12 is applied to the palm of the deformed or contracted hand, and the finger retainers 16*a*–16*e* are wrapped around the corresponding five fingers. The hooking element 20 of the VELCRO fastener at the free end of each of the finger retainers is then pressed into engagement with the mating looping element 18.

Figure 10:
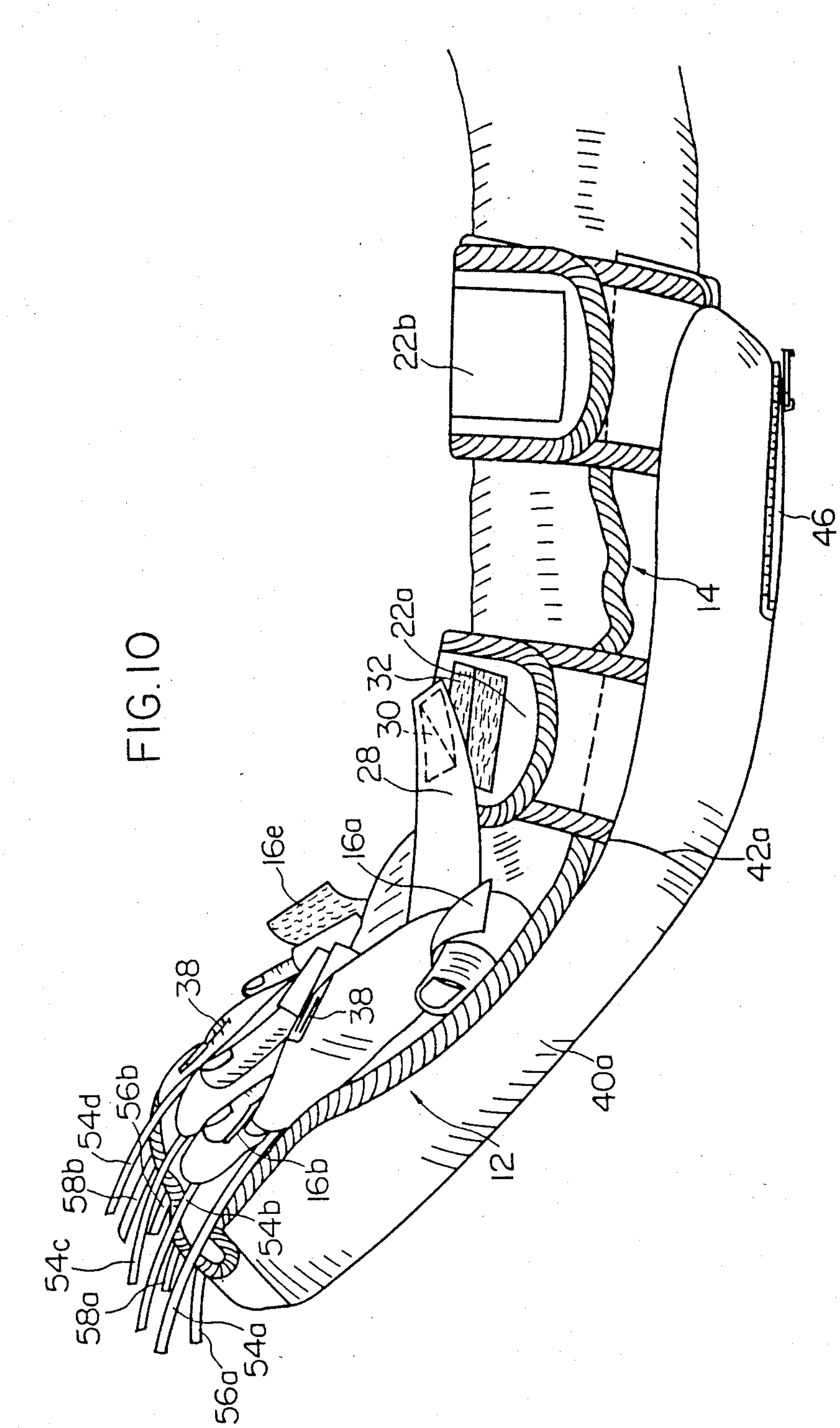
FIG. 10 is a perspective view of the appliance applied to the hand with the first and second pockets partially bent backward.
Figure 11:
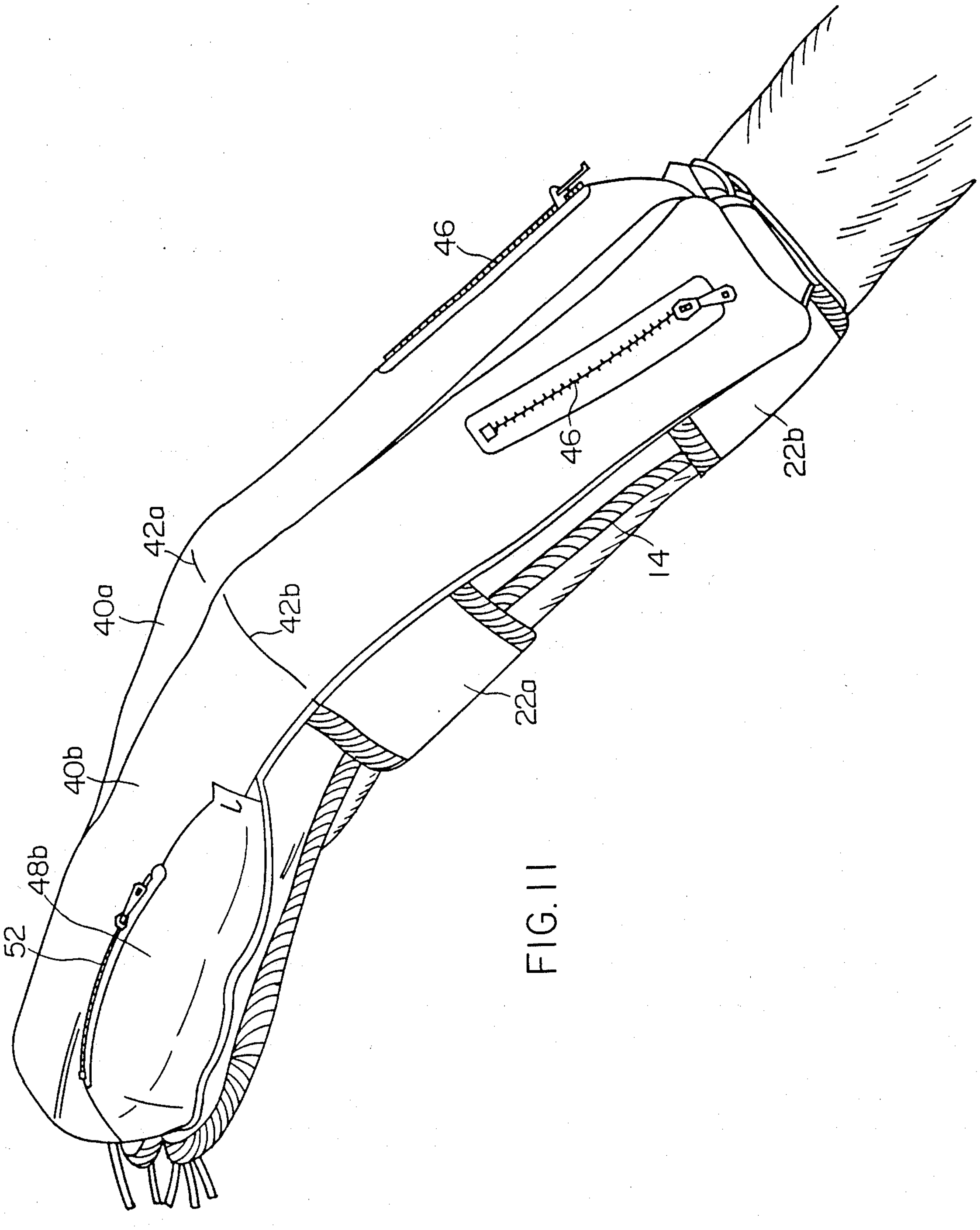
FIG. 11 is a perspective view of the appliance applied to the hand as viewed from the palm side.

The wrist and forearm retainers 22*a*, 22*b* are wrapped around the wrist and forearm and the hooking elements 26 of the VELCRO fasteners are pressed against the mating looping elements 24. The bracer band 28 is passed from between the thumb and forefinger to the wrist and the hooking element 30 of the VELCRO fastener at the free end of the bracer band is pressed against the looping element 32 (FIGS. 9 and 10) on the outer surface of one of the straps of the wrist retainer 22*a*.

With the five fingers and forearm thus held in place in the therapeutic appliance (FIG. 9), the compressed air source 64 is operated to introduce compressed air at a predetermined pressure through the air hose 62 and air tubes **54*a*–54*d*, 56*a*, 56*b* and 58*a*, 58*b* into the air bladders 36*a*, 44*a* and 50*a*** to inflate the bladders to thereby expand the respective pockets, whereby the thumb, forefinger, middle finger, ring finger and little finger are laterally spread apart from each other while at the same time the hand is bent backwards with its thumb and fingers extended straight.

More specifically as to the bending action, the long pockets **40*a*, 40*b* on the palm side of the splint cloth 10 are provided transversely at a location corresponding to the wrist with the darts 42*a*, 42*b*** so designed as to permit the pockets when expanded to be bent in a V-shape at an angle corresponding to the angle at which the hand of a healthy person is normally bent toward the back of the hand around the carpal joint.

As the bladders **44*a* and hence the pockets 40*a*, 40*b* are expanded, the pockets 40*a*, 40*b* are bent in a shallow V-shape to forcedly bend the hand backwards. During the bending action, the wrist pad 66 retains the wrist fixed in place while the palm pad 72 presses against the hollow of the palm of the patient's hand to positively transmit the urging action of the pockets 40*a*, 40*b* to the palm. In this way, the wrist pillow 66 and palm pad 72 aid in the actions of the pockets 40*a* 40*b* and the pockets 48*a*, 48*b*** to extend and bend the fingers and hand.

It is thus to be appreciated that the pockets **34*a*–34*d*, 40*a*, 40*b* and 48*a*, 48*b***, when expanded, cooperate to spread apart the fingers while extending the fingers and bending the fingers and carpal joint.

After compressed air is supplied to maintain the bladders **36*a*–36*d*, 44*a* and 50*a*** inflated for a predetermined period of time (e.g. ten to thirty seconds), the air is forcedly discharged from the bladders to allow the fingers and wrist to return to their original contracted positions. After the finger joints and carpal joint are held in their contracted positions for several to ten seconds, compressed air is again supplied to inflate the bladders. These cyclic operations may be repeated usually ten to twenty or more times to impart repeated spreading, extending and backwardly bending motions to the fingers and hand. Sometimes, pressurization of the bladders may be continued arbitrarily for a relatively long time without setting the time beforehand. As the patient becomes accustomed to such exercise, the number of repetitions of the operation as well as the time of pressurization may be increased.

The method of using the appliance described above is intended to extend and open up the hand, fingers and carpal joint to remedy the bent contracture and dysfunction in extending motion by inflating and deflating all of the bladders. However, in the case that the bending contracture or dysfunction in extending and flexing motion has not extended to all of the carpal joint, hand and fingers, any one or more of the air supply tubes leading to unnecessary bladders may be closed as by the use of pinch clip to selectively remedy the affected parts only.

When the treatment is completed, the finger retainer means **16*a*–16*e* and the wrist and forearm retainer means 22*a*, 22*b*** are released, whereby the therapeutic appliance may be easily removed from the hand, fingers and forearm.

Rythmical and intermittent stimuli imparted in a sustained manner to the affected carpal joint, hand and fingers by extending and bending the same, as well as opening up the fingers, will be transmitted through the sensory nerves to the sensory and perceptive system of the nerve center and thence through the nervous tissues in the nerve center to the motor system to induce and promote the plasticity and compensatory function of the nervous system whereby the voluntary motions at the treated locations may be developed and promoted.

From the foregoing description, it is to be understood that the therapeutic appliance according to the present invention is capable of providing drastically enhanced effects of extending and spreading apart the hand, fingers and carpal joint, particulary owing to the provision of the three-dimensionally sewn pockets **40*a*, 40*b***, as compared to the prior art applicance having two-dimensionally sewn pockets, and is capable of helping a patient recover the functions of his or her incapacitated hand and fingers through the use of the appliance for a relatively short period of time.

What is claimed is:

1. A therapeutic appliance for improving functions of a person's carpal joints, hand and five fingers, comprising:

(a) a splint cloth made of flexible material and including
   (i) a palm splint portion accommodating a palm with the fingers spread apart, and
   (ii) a forearm splint portion extending from the palm splint portion to cover an underside surface of the carpal joint and forearm;

(b) first retainer means disposed on the hand back side surface of said palm splint portion for releasably holding the five fingers individually in their spread apart positions;

(c) second retainer means on said forearm splint portion for releasably securing at least one of the wrist and forearm to the forearm splint portion;

(d) a plurality of first generally delta-shaped pockets made of substantially non-extensible material disposed on the hand back side surface of said palm splint portion, each positioned between adjacent fingers;

(e) a pair of second pockets made of substantially non-extensible material disposed on the palm side surface of said splint cloth and extending in generally parallel relation to each other form tips of the fingers toward the forearm along substantially the full length of the splint cloth, said second pockets positioned so as to span the space between the thumb and the forefinger and the space between the middle finger and the ring finger, respectively;

(f) a pair of third generally delta-shaped pockets made of substantially non-extensible material disposed on the palm side surface of said palm portion, one of said third pockets extending between said pair of second pockets from the finger tips toward the wrist so as to span the forefinger and the middle finger, and the other of said third pockets extending from the finger tips toward the wrist so as to span the ring finger and the little finger;

(g) a plurality of inflatable bladders, one accommodated within each of said first, second and third pockets; and (h) fluid supply and discharge tubes connected to said bladders for supplying and discharging fluid at a predetermined pressure to and from said bladders, wherein said pair of second pockets is provided with darts at locations corresponding generally to the wrist so as to facilitate bending of said second pockets back toward the palm side when the bladders within said second pockets are inflated with fluid.

2. A therapeutic appliance according to claim 1, further comprising a wrist pillow detachably secured to the hand back side surface of said forearm splint portion at a location corresponding to the wrist.

3. A therapeutic appliance according to claim 1, further comprising a palm pad detachably secured to the hand back side surface of said palm splint portion so as to fit the hollow of the palm.

4. A therapeutic appliance according to claim 2, further comprising a palm pad detachably secured to the hand back side surface of said palm splint portion so as to fit the hollow of the palm.

* * * * *